United States Patent [19]

Tseo et al.

[11] Patent Number: 4,527,588

[45] Date of Patent: Jul. 9, 1985

[54] SAFETY VALVE

[75] Inventors: Gus G. Tseo, San Diego; Mark E. Alpen, Escondido, both of Calif.

[73] Assignee: Warner-Lambert Company, Morris Plains, N.J.

[21] Appl. No.: 561,481

[22] Filed: Dec. 14, 1983

[51] Int. Cl.³ ............... F04B 43/12; F16K 31/58
[52] U.S. Cl. ............................. 137/565; 251/6; 251/342; 251/349
[58] Field of Search .......... 137/565, 843, 853; 251/6, 9, 342, 343, 349, 369

[56] References Cited

U.S. PATENT DOCUMENTS

| 384,306 | 6/1888 | Bourdil | 137/853 |
|---|---|---|---|
| 1,418,592 | 6/1922 | McGee | 251/342 |
| 2,425,901 | 8/1947 | Thomas | 251/342 |
| 2,694,379 | 11/1954 | Hein | 251/342 |
| 2,723,678 | 11/1955 | Wilson | 137/493 |
| 3,384,113 | 5/1968 | Pennisi | 137/525 |
| 3,692,071 | 9/1972 | Begleiter | 141/313 |
| 3,717,174 | 2/1973 | DeWall | 137/565 |
| 3,759,289 | 9/1973 | DeWall | 137/525 |
| 3,800,799 | 4/1974 | McWhorter | 251/342 |
| 3,802,662 | 4/1974 | Viguier | 251/342 |
| 3,865,133 | 2/1975 | Alford | 137/512 |
| 3,938,909 | 2/1976 | Willock | 251/9 |
| 3,955,594 | 5/1976 | Snow | 137/493 |
| 3,977,409 | 8/1976 | Brendling | 251/342 |
| 4,056,116 | 11/1977 | Carter et al. | 251/342 |
| 4,142,845 | 3/1979 | Lepp et al. | 251/9 |
| 4,357,959 | 11/1982 | Shetler | 137/853 |

FOREIGN PATENT DOCUMENTS 1078392  3/1960  Fed. Rep. of Germany ...... 251/342

Primary Examiner—Alan Cohan
Assistant Examiner—John A. Rivell
Attorney, Agent, or Firm—Neil K. Nydegger

[57] ABSTRACT

A safety valve in combination with a resilient tube for preventing the free flow of fluid through the resilient tube comprises a valve body which is connected to a valve head of generally circular cross-section which is formed with a flat peripheral land. The resilient tube is disposed over the valve head for snug fluid-sealing engagement between the inner surface of the tube and the flat land on the valve head. Also, the resilient tube is fluid sealed to the valve body for fluid communication therebetween. Stretching the resilient tube separates a portion of the inner surface of the tube from the flat land on the valve head to permit fluid flow past the valve head. When the resilient tube is unstretched, the engagement between the inner surface of the tube and the flat land of the valve head prevents free fluid flow.

8 Claims, 7 Drawing Figures

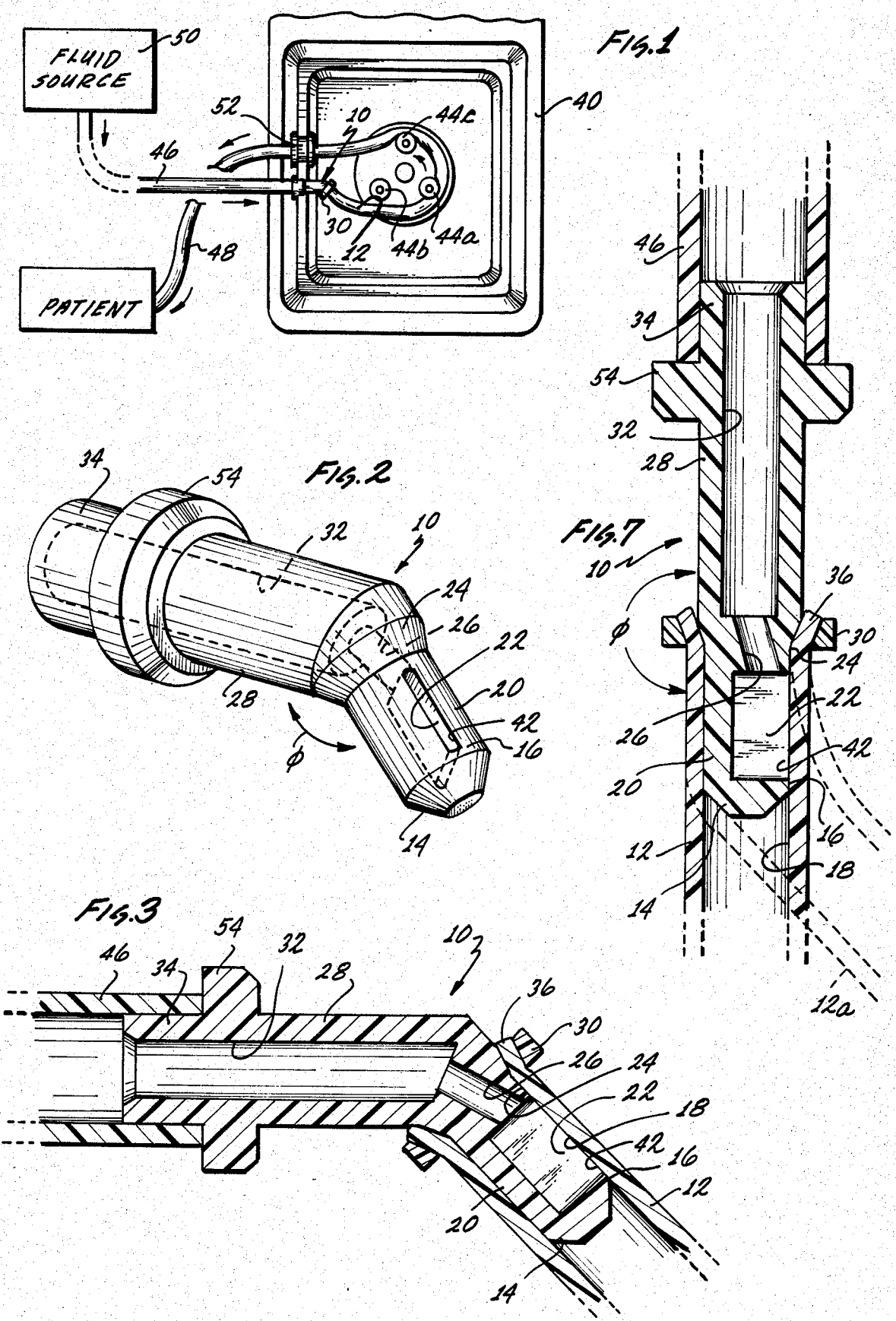

SAFETY VALVE

BACKGROUND OF THE INVENTION

This invention relates generally to safety valves. More specifically, the present invention relates to devices which are useful for the control of free fluid flow conditions in resilient tubing. This invention is particularly, but not exclusively, suited for use with a peristaltic pump to allow for flow through the associated tubing during pumping conditions and to prevent flow through such tubing when the tubing is disconnected from the pump.

DESCRIPTION OF THE PRIOR ART

The use of pumps to control and assist in the enteral or parenteral infusion of fluids into the body of a mammal is well known. Nevertheless, there is the persistent need to improve these pump systems to make them more reliable, accurate and easy to use. One particularly troublesome problem in pump systems which have no valving in the fluid line has been the need for a device which automatically prevents the unwanted flow of IV fluid to a patient. The problem is particularly apparent where use of a peristaltic pump is involved.

Often, peristaltic pumps employ a continuous tube connection between the fluid source and the patient. In a typical peristaltic pump system, the fluid line, or tube, is associated with some drive means that applies a peristaltic action to the tube for movement of fluid through the tube. Obviously, the pumping operation itself is a means for controlling fluid flow. When, however, the tubing is disconnected from the peristaltic pump, there is no means in the fluid line to automatically control or inhibit the fluid flow. Instead, a free flow condition is established. Such a free flow condition can allow unwanted infusion of fluids to the patient unless properly controlled. Free flow can be a particularly undesirable situation where parenteral infusion is involved.

Various devices have been proposed to control the unwanted flow of fluid through an IV tubing set that is being used with a pump or a controller. Pinch clamps well known in the art are typical of such devices. These clamps are generally associated directly with the exterior surface of the tube and are manipulated independently of the pump or controller. However, other clamps also well known in the art may be directly associated with the operation of the pumping or controlling device. Furthermore, such clamps may even be a functional part of the device.

When independent clamps are employed to control free flow, they must be engaged prior to disconnecting the tubing from the pump or controller or a free flow condition will be established. Moreover, closure of the tube to prevent free flow requires an independent conscious act on the part of the operator. Even in the embodiments where a clamp is employed directly with a pump or controller, a free flow condition still exists whenever the tube is separated from the device unless the clamp itself or some other valving means is employed in the fluid line. Generally, however, these flow control devices act externally on the tubing.

As mentioned above, in a peristaltic pump the possibility of free flow is particularly prevalent. Indeed, the peristaltic action requires an unobstructed fluid line for its operation. On the other hand, whenever a free flow condition is undesirable the line needs to be closed. Accordingly, it is an object of the present invention to provide a self-actuating device for controlling the free flow of a fluid through a resilient tube. It is another object of this invention to provide a safety valve that is integrally positioned in the fluid line to permit fluid flow in the presence of a peristaltic action and to prevent fluid flow when such action ceases or the tube is separated from the pump. It is yet another object of the present invention to provide a safety valve which is reliable, easy to use and inexpensive.

SUMMARY OF THE INVENTION

A preferred embodiment of the novel safety valve includes a valve body formed with a fluid passageway therethrough and having an inlet and an outlet. Formed onto the valve body intermediate between the inlet and the outlet is a shoulder. Extending from the valve body is a neck portion having a fluid chamber in fluid communication with the outlet and having a generally circular cross-sectional valve head whose periphery is a flat land. A resilient tube is disposed over the neck portion and the valve head and is seated against the shoulder of the valve body to establish a fluid seal therewith. So disposed, the tube is also positioned over the valve head to provide a snug fit between the inside surface of the tube and the flat land on the valve head to prevent fluid flow past the valve head. As the resilient tube is pulled transverse to the valve head axis, a portion of the inside surface of the tube is separated from the flat land to allow fluid communication from the passageway and through the fluid chamber into the extension of the tube. When the resilient tubing is relaxed, the inside surface of the resilient tubing returns to its previous unstretched position and fits in snug engagement with the flat land portion on the neck to prevent fluid flow from the fluid chamber into the extension of the tube.

The novel features of this invention as well as the invention itself, both as to its organization and operation, will be best understood from the accompanying drawings taken in conjunction with the accompanying description in which similar reference characters refer to similar parts and in which:

BRIEF DESCRIPTION OF THE DRAWINGS

FIG. 1 is a schematic view of a peristaltic pump incorporating the present invention in an operational environment;

FIG. 2 is a perspective view of an embodiment of the present invention with certain portions shown in phantom to indicate inner cavities;

FIG. 3 is a side cross-sectional view of the device of FIG. 2 shown with attached tubing sections;

FIG. 7 is a cross-sectional side view of yet another alternate embodiment of the present invention with associated tubing and a phantom view of tubing in the stretched position.

DESCRIPTION OF THE PREFERRED EMBODIMENT

Figure 4:
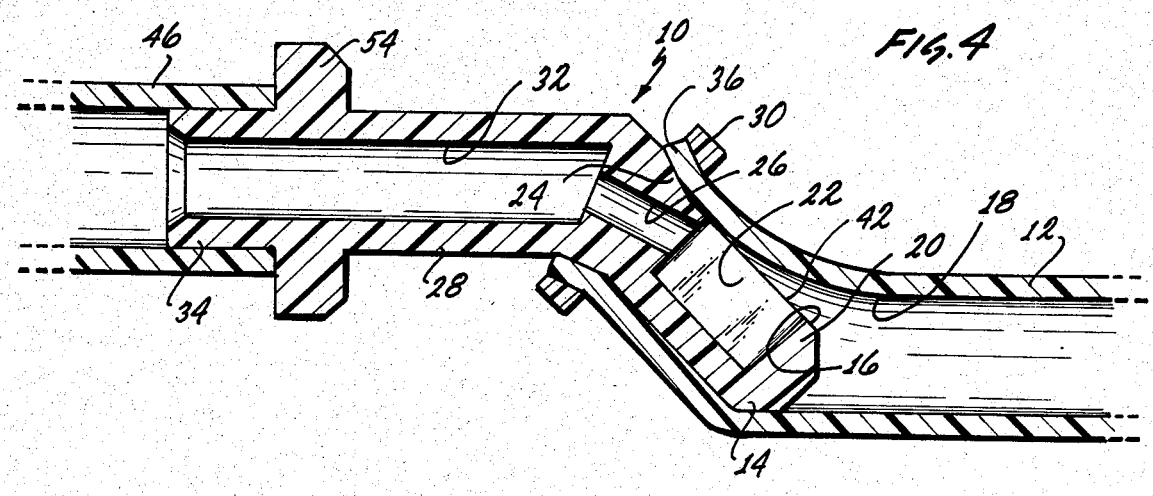
FIG. 4 is a cross-sectional side view of the device in FIG. 3 shown with the tubing section stretched.

Referring to FIG. 1 the safety valve generally designated 10 is shown in combination with a rotary peristaltic pump 40. As shown in FIG. 1 a fluid source 50 is connected in fluid communication by tube 46 with the safety valve 10. The connection between tubing set 46 and safety valve 10 is accomplished by any means well known in the art. Also attached to safety valve 10, again by any means well known in the art, is a resilient tube 12. As shown in FIG. 1, resilient tube 12 is passed around the rotors 44a, b and c of peristaltic pump 40 and is then connected through a fitment 52 to a tubing set 48 which is in fluid communication with the patient.

As is best seen in FIG. 2, the safety valve 10 comprises a valve body 28 which is formed with a fluid passageway 32 having an inlet 34 and an outlet 26. Integrally connected with the valve body 28 is a neck 20 having a fluid chamber 22 formed therein which is in fluid communication with the outlet 26 of valve body 28. Also shown in FIG. 2 is an outlet port 42 associated with fluid chamber 22 which will allow fluid flow through safety valve 10 from inlet 34 to outlet port 42. In the preferred embodiment, the neck portion 20 is connected with the valve body 28 at an angle $\phi$. As can be easily appreciated, the angle $\phi$ may take on any range of values from approximately 110° through 180°. It should be understood, however, that angle $\phi$ is not limited by any specified range of values. Instead, the value of angle $\phi$ depends upon the particular needs of the system in which safety valve 10 is to be used. For example, an embodiment of the safety valve 10, as shown in FIG. 7, illustrates an application where angle $\phi$ is 180°. It should also be appreciated by those skilled in the pertinent art that safety valve 10 can be formed from a number of materials, and no limitation on the type of material to be used for safety valve 10 is intended. Nevertheless, for the purposes of use in medical devices and for use with the peristaltic pump as intended in the preferred embodiment, a suggested material is Styrene Acryli Nitrile (SAN) manufactured by Dow Corning as Tyril 860B.

Referring now to FIG. 3, it is seen that the safety valve 10 is adaptable for connection with tubing sets. Specifically, in FIG. 3 at the inlet 34 end of valve body 28, a tubing set 46 is operatively associated with safety valve 10 to establish a fluid seal around inlet 34 and permit fluid communication between tubing set 46 and safety valve 10. Connection of tube 46 with safety valve 10 may be accomplished by any means well known in the art, such as by solvent bonding. As also shown in FIG. 3, the tube 46 is shown abutting retention ring 54 to improve the fluid seal between tube 46 and valve body 28. The retention ring 54 provides another function in that it is useful for connecting safety valve 10 with a retaining slot (not shown) on the face of pump 40. It should also be recognized that tube 46 can be connected to inlet 34 at the inner surface of passageway 32. This connection (not shown) would place safety valve 10 in a surrounding relationship to the end of tube 46 at their point of connection.

Also attached to safety valve 10 is the resilient tube 12. Connection of the resilient tube 12 with safety valve 10 is accomplished by slidably disposing the neck 20 of safety valve 10 into the resilient tube 12. With neck 20 inside resilient tube 12, the tube end 36 is held in snug engagement with shoulder 24 by retaining collar 30 to provide a fluid seal between safety valve 10 and tube end 36. The positioning of neck 20 into resilient tube 12 also allows the inner surface 18 of resilient tube 12 to be disposed in snug engagement with the peripheral land 16 of neck 20. The only exception to this engagement for the embodiment shown in FIG. 2 occurs where outlet port 42 opens from fluid chamber 22.

Figure 5:
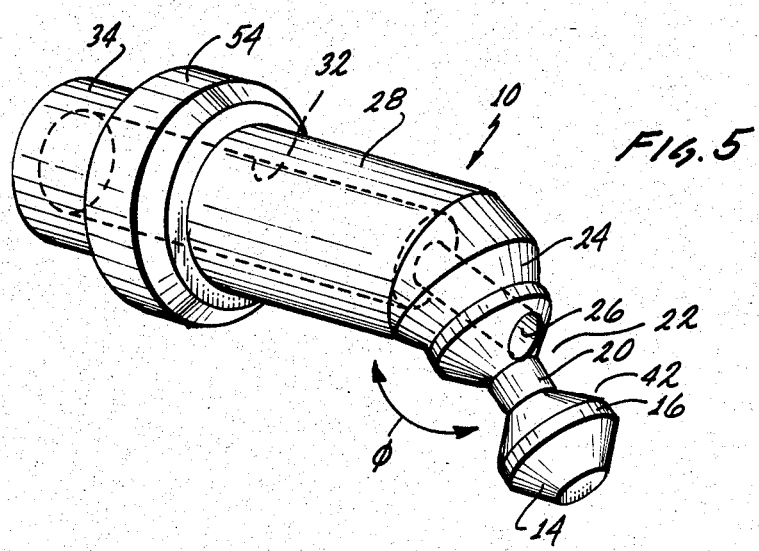
FIG. 5 is a perspective view of an alternate embodiment of the present invention with portions shown in phantom to indicate internal cavities.
Figure 6:
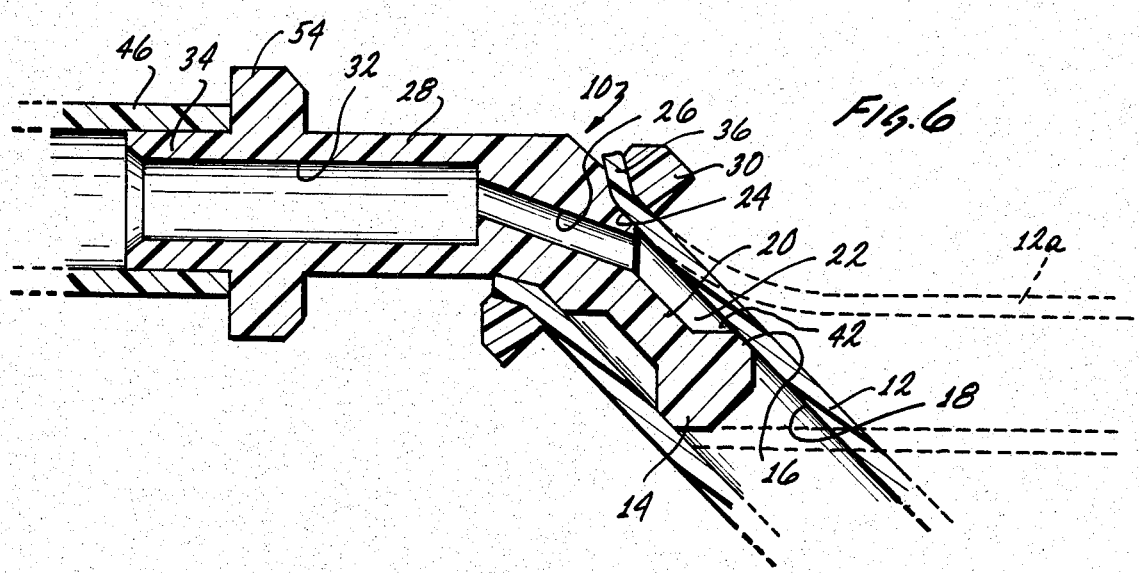
FIG. 6 is a side cross-sectional view of the device shown in FIG. 5 with attached tubing and a phantom view of stretched tubing.

As seen in FIG. 2 and in the alternate embodiment in FIG. 5, the peripheral land 16 is formed around neck 20 and is specifically dimensioned to provide a snug engagement between the inner surface of resilient tube 12 and the peripheral land 16 of neck 20. With this structure the inner surface 18 of resilient tube 12 rests against peripheral land 16 of neck 20 and provides a fluid seal to prevent fluid flow from fluid chamber 22 through outlet port 42 and into the resilient tube 12. As can be seen by reference to FIG. 4 and FIG. 6, depending on the particular embodiment, upon a stretching of resilient tube 12 in a direction transverse to the axis of neck 20, the inner surface 18 of resilient tube 12 separates from portions of peripheral land 16 to provide for fluid communication through the safety valve 10 from tube 46 to the resilient tube 12. It should be noted that such fluid flow can be achieved whenever resilient tube 12 is stretched in any direction which will lift the inner surface 18 of resilient tube 12 away from the flat land 16 of valve head 14 as shown with an alternate embodiment of the invention in FIG. 6 or from the vicinity of outlet port 42 as shown with the preferred embodiment of the invention in FIG. 4. In a peristaltic pump, with the embodiments shown in FIG. 2 and FIG. 3 the most efficient direction of stretch is in a direction substantially parallel to the longitudinal axis of fluid passageway 32.

An alternate embodiment of the present invention, which was previously alluded to, is shown in FIG. 5. In this particular embodiment of the present invention, a portion of the neck 20 is of reduced dimensions to form a valve head 14 at the distal end of neck 20. In this particular embodiment, the fluid chamber is defined by the space between valve head 14 and the shoulder 24. In all important particulars the alternate embodiment of the present device shown in FIG. 5 functions in substantially a similar manner for the above described embodiment shown in FIG. 2. As with the preferred embodiment, the alternate embodiment allows for the connection and fluid sealing between safety valve 10 and resilient tube 12 by use of a retaining collar 30 engaged at shoulder 24 of safety valve 10. In the alternate embodiment, fluid is retained in the fluid chamber 22 by the snug connection between resilient tube 12 and the peripheral land 16 on valve head 14 whenever resilient tube 12 is in the relaxed or unstretched condition. However, as can be appreciated by reference to FIG. 6, whenever resilient tube 12 is stretched to a position such as indicated by the character 12a, the inner surface 18 of resilient tube 12 separates from a portion of peripheral land 16 on valve head 14 and permits fluid communication through safety valve 10 from the tube 46 to the extension of resilient tube 12. Like the preferred embodiment, the alternate embodiment shown in FIG. 5 and FIG. 6 allows for an angle $\phi$ between the longitudinal axis of the fluid passageway 32 in safety valve 10 and the neck portion 20 of safety valve 10.

In still another embodiment of the present invention, the angle $\phi$ may be 180°. In this configuration the longitudinal axis of fluid passageway 32 is coaxial with the longitudinal axis of the neck 20. As shown in FIG. 7, the action of the structural parts of safety valve 10 is as previously described for the preferred embodiment shown in FIG. 2 and the alternate embodiment shown in FIG. 5.

In operation, the safety valve 10 is incorporated into a tubing system as described above. With a peristaltic pump, the resilient tube 12 is placed in operative association with the rotors 44a, b and c of a peristaltic pump 40 as shown in FIG. 1. In this configuration the placement of safety valve 10 and tube 12 on pump 40 applies the stretching action on tube 12 to separate its inner surface 18 from the peripheral land 16 of safety valve 10 to permit fluid flow through the tube 12. From the drawings, the operation of the apparatus of the present invention can be appreciated. For example, placement of valve 10 onto pump 40 as shown in FIG. 1 will initially configure tube 12 relative to valve 10 in a manner as shown in FIG. 3. Subsequent engagement of the tube 12 with rotors 44 a, b and c as shown in FIG. 1 will configure tube 12 relative to valve 10 in a manner as shown in FIG. 4. With tube 12 and valve 10 configured as shown in FIG. 4, fluid can flow through valve 10 and the pump 40 will be operative. Several variables will, of course, determine whether tube 12 separates from valve 10 to permit fluid flow. For instance, in the case where valve 10 is placed on pump 40 as shown in FIG. 1, it is easily appreciated that as the angle $\phi$ (see FIG. 2) is decreased from an obtuse angle to a right angle, the more likely it is that engagement of tube 12 with rotors 44 a, b and c will cause separation of tube 12 from the land 16 of valve 10. As will be appreciated by the skilled artisan, a value for the angle $\phi$ between neck portion 20 and valve body 28 can be selected which will ensure that placement of valve 10 on pump 40 and the engagement of tube 12 with rotors 44a, b and c will separate the inner surface 18 from peripheral land 16 of safety valve 10 to permit fluid flow through the tube 12. Since the pump 40 in its normal operation is the means which stresses or stretches the tube to keep the valve open for metered fluid flow, it follows that if the tube inadvertently "jumps" off the pump rotors 44a, b and c, the resilient tube 12 will relax and revert immediately to its normal condition and the valve will close smartly avoiding dangerous uncontrolled free flow.

It should also be appreciated that any means capable of stretching tube 12 can be employed to allow fluid flow through the system. Such a means can include manual operation. In any case, when there is no longer a stretching action on resilient tube 12, safety valve 10 will prevent fluid flow through the resilient tube 12. From the foregoing it can be appreciated that in accordance with the present invention, fluid pressure does not provide the force to open safety valve 10. Instead it is the stretching action on resilient tube 12 that accomplishes this function. It follows that a relaxed resilient tube 12 will prevent such flow.

While a particular safety valve as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the apended claims.

We claim:

1. A safety valve for permitting the flow of fluid through a resilient tube operatively associated with a fluid flow device comprises:
   a valve body formed with a fluid passageway therethrough having an inlet and an outlet;
   a valve head formed with a peripheral land and connected to said valve body with the outlet intermediate the inlet and said valve head;
   a resilient tube attached to said valve body for fluid communication with said outlet and disposed around said valve head for fluid sealing engagement between the inside surface of said tube and the surface of said land on said valve head when said tube is disengaged from the fluid flow device;
   means for fixedly connecting said valve body relative to the fluid flow device; and
   means for engaging said tube with the fluid flow device to distort said tube in a direction transverse to the surface of said land to disengage a portion of the inner surface of said tube from said land to permit fluid flow through said tube.

2. A safety valve as cited in claim 1 wherein the fluid flow device is a rotary peristaltic pump operatively associated with said resilient tube and said valve.

3. A safety valve as cited in claim 1 further comprising a neck rigidly connecting said valve head with said body to form a fluid chamber within said tube between the outlet and said valve head.

4. A safety valve as cited in claim 1 wherein said valve head is angled relative to said valve body.

5. A safety valve as cited in claim 3 wherein said neck is angled relative to said valve body.

6. A safety valve as cited in claim 1 wherein said outlet port defines an opening intersecting a portion of said peripheral land.

7. A safety valve as cited in claim 1 wherein said outlet port defines an annular undercut in said peripheral land.

8. A method of providing an automatic safety valve in a continuous fluid flow system including a fluid flow device connected to a flexible, resilient tube comprising the steps of:
   a. inserting a relatively rigid valve in series with said tube to make a fluid tight seal between a portion of said rigid valve and said tube, said rigid valve having a port normally closed by said seal;
   b. fixedly mounting said valve on the fluid flow device; and
   c. engaging a portion of the tube external to said valve with the fluid flow device to cause tube distortion effective to break the seal and open said port for operation of the fluid flow device.

* * * * *